United States Patent [19]
Sode

[11] Patent Number: 6,103,509
[45] Date of Patent: Aug. 15, 2000

[54] MODIFIED GLUCOSE DEHYDROGENASE

[75] Inventor: Koji Sode, Tokyo, Japan

[73] Assignee: Lifescan Inc., Milpitas, Calif.

[21] Appl. No.: 08/923,109

[22] Filed: Sep. 4, 1997

[30] Foreign Application Priority Data

Mar. 3, 1997 [JP] Japan .................... 9-061727

[51] Int. Cl.[7] .................... C12N 9/04
[52] U.S. Cl. .................... 435/190; 435/320.1; 435/14; 435/252.3; 536/23.2
[58] Field of Search .................... 435/14, 252.3, 435/190, 320.1; 536/23.2

[56] References Cited

U.S. PATENT DOCUMENTS 5,804,047   9/1998   Karube et al. .................... 204/403

OTHER PUBLICATIONS

A.M. Cleton–Jansen, N. Goosen, G. Odle and P. van de Putte, *Nucleic Acids Research*, vol. 16 No. 13, p.6228 (1988).

A.M. Cleton–Jansen, N. Goosen, T. Wenzel and P. van de Putte, *Journal of Bacteriology*, vol. 170, No. 5, p. 2121–2125 (May 1988).

A.M. Cleton–Jansen, Sylvia Dekker, P. van de Putte, and N. Goosen, *Mol Gen Genet*, vol. 229, p. 206–212 (1991).

A.M. Cleton–Jansen, N. Goosen, Olivier Fayet, and P. van de Putte, *Journal of Bacteriology*, vol. 172, No. 11, p. 6308–6315 (Nov. 1990).

Minoru Ameyama, Emiko Shinagawa, Kazunobu, Matsushita and Osao Adachi, *Agric. Biol. Chem*, 45(4), p.851–861 (1981).

Minoru Ameyama, Masatsugu Nonobe, Emiko Shinagawa, Kazunobu Matsushita, Koichi Takimoto and Osao Adachi, *Agric. Biol. Chem*, 50(1), p. 49–57 (1986).

Paul Dokter, Johannes Frank, Jzn. and Johannis Duine, *Biochem Journal*, vol. 239, p. 163–167 (1986).

Kazunobu Matsushita, Emiko Shinagawa, Osao Adachi and Minoru Ameyama, *FEMS Microbiology Letters* vol. 55, p. 53–58 (1988).

Mamoru Yamada, Kenichi Sumi, Kazunobu Matsushita, Osao Adachi, and Yasue Yamada, *The Journal of Biological Chemistry*, vol. 268, No. 17, p. 12812–12817, (Jun. 15, 1993).

Cozier GE, et al. "Structure of the quinoprotein glucose dehydrogenase of *Escherichia coli* modelled on that of methanol dehydrogenase from Methylobacterium extorquens" Biochem J., 1995, vol. 312, pp. 679–685, Dec. 15, 1995.

Cleton–Jansen AM, et al "Cloning, characterization and DNA sequencing of the gene encoding the Mr 50,000 quinoprotein glucose dehydrogenase from Acinetobacter calcoaceticus" Mol Gen Genet., 1989, vol. 217, pp. 430–436, Jun. 1, 1989.

*Primary Examiner*—Ponnathapu Achutamurthy
*Assistant Examiner*—Bradley S. Mayhew

[57] ABSTRACT

The invention provides a modified pyrrolo-quinoline quinone glucose dehydrogenase (PQQGDH) enzyme protein which is modified to have a substrate specificity to glucose. The modified PQQGDH of the invention exhibits a high substrate specificity compared to the wild type PQQGDH, thus is useful in determining glucose concentration in clinical assays and food analyses. A gene coding for the modified PQQGDH and a glucose sensor comprising the modified PQQGDH are also disclosed.

11 Claims, 2 Drawing Sheets

MODIFIED GLUCOSE DEHYDROGENASE

BACKGROUND OF THE INVENTION

This application is claiming a priority based on a Japanese Patent Application No. 61727/97 filed on Mar. 3, 1997. The contents of the patent application are incorporated herein by reference.

This invention relates to a modified pyrrolo-quinoline quinone (PQQ) glucose dehydrogenase (GDH). The enzyme of the invention exhibits an improved substrate specificity, thus is useful for measurement of glucose in clinical assays and food analyses.

Glucose is present in the blood and has been utilized as an important marker of diabetes. Also, in fermentation with the use of microorganisms, the measurement of glucose as growth media for microorganisms is an important parameter in process monitoring. Glucose has been assayed by enzymatic methods using glucose oxidase (hereinafter referred to as GOD) or glucose 6-phosphate dehydrogenase (hereinafter referred to as G6PDH). In the method with the use of GOD, however, it is necessary to add catalase or peroxidase to the analysis system, which catalyzes hydrogen peroxide formed through the glucose oxidation reaction, in order to induce the color development reaction. Further, attempts have been made to develop biosensors with the use of GOD. In these biosensors, however, the enzyme reaction depends on the concentration of oxygen dissolved in an aqueous solution. Thus they are unsuitable for samples with high glucose concentration or could provide data including errors depending on the dissolved oxygen concentration. On the other hand, G6PDH has been employed in the assay of glucose by a spectrochemical method. However, this method involves a troublesome procedure of adding a coenzyme NAD(P) to the reaction system.

Recently, the use of a novel enzyme PQQGDH has been noted as an alternative to the enzymes employed in the conventional methods for enzymatic assay of glucose. Since PQQGDH is an enzyme bearing a coenzyme bound thereto and does not require oxygen as an electron acceptor, this enzyme is expected to be applicable in the field of analysis, for example, as a recognition element of a glucose sensor. In particular, the structural gene of glucose dehydrogenase PQQGDH derived from E. coli and bearing pyrrolo-quinoline quinone as a coenzyme was known [AM. Cleton-Jansen et al., J. Bacteriol. (1990) 172, 6308–6315], and its heat stability could be improved [K. Sode et al., FEBS Lett. (1995) 364, 325–327], thus the PQQGDH of E. coli is expected to be suitable for various applications. However, the PQQGDH derived from E. coli has a problem in its substrate specificity. Namely, it reacts not only with glucose but also other saccharides [Ameyama et al., Agric. Biol. Chem. (1986) 50, 49–57].

It was previously reported that a mutated enzyme, wherein the histidine 787 residue had been spontaneously mutated into an asparagine residue in the structural gene of the PQQGDH of Gluconobacer oxydans (hereinafter referred to as G. oxydans), had a lower substrate specificity and higher reactivities with saccharides other than glucose, compared with the wild type PQQGDH of G. oxydans [AM. Cleton-Jansen et al., Mol. Gen Genet. (1991) 229, 206–212]. It is therefore believed that this site would play an important role in the substrate recognition by the PQQGDH of G. oxydans. On the other hand, the histidine 787 residue in the PQQGDH of G. oxydans corresponds to the 775 amino acid residue in the PQQGDH of E. coli, which is also a histidine residue [G. E. Cozier and C. Anthony, Biochem. J. (1995) 312, 679–685]. The PQQGDH of G. oxydans scarcely reacts with saccharides other than glucose [Ameyama et al., Agric. Biol. Chem. (1981) 45, 851–861], while the PQQGDH of E. coli can react with other saccharides. Based on these observations, the histidine 775 residue in the PQQGDH of E. coli is considered to be different in its role in determining the substrate specificity from the histidine 787 residue in the PQQGDH of G. oxydans. Accordingly, it was not possible in any way to estimate changes in the properties of the enzyme caused by substituting the histidine 775 residue in the PQQGDH of E. coli with other amino acids.

SUMMARY OF THE INVENTION

The present invention provides a modified pyrrolo-quinoline quinone glucose dehydrogenase (PQQGDH) enzyme protein which is modified to have a substrate specificity to glucose. More particularly, the invention provides a modified PQQGDH enzyme protein modified to have a substrate specificity to glucose wherein the histidine residue in a region corresponding to the region from Ala772 to Phe778 of *Escherichia coli* PQQGDH is substituted with an amino acid residue other than histidine.

In one aspect of the invention, a modified PQQGDH having mutations in PQQGDH derived from E. coli, is provided. The modified PQQGDH of the invention has an extremely high substrate specificity, thus is suitable for using clinical assays and food analyses. In accordance with the invention, modified PQQGDH enzyme protein produced from a modified PQQGDH structural gene scarcely reacts with saccharides other than glucose, and maintains a high activity of glucose oxidization, thereby allowing highly sensitive and highly selective measurement of glucose.

In another aspect of the invention, a modified PQQGDH structural gene encoding a modified PQQGDH enzyme protein is provided. In the modified PQQGDH enzyme protein coded by the gene, the histidine 775 residue in the region of the amino acids 772 to 778 (-Ala-Gly-Gly-His-Gly-Ser-Phe-) (SEQ ID NO:10) of the amino acid sequence of the PQQGDH of E. coli has been substituted with another amino acid residue. Preferably, His775 is substituted with an amino acid residue selected from asparagine, aspartlc acid, serine, tyrosine, lysine, leucine, tryptophane, glutamic acid and glutamine.

According to the present invention, when the amino acid residue 775 in the PQQGDH of E. coli is substituted with an asparagine residue, the substrate specificity of the modified PQQGDH was increased. This effect was exactly the opposite of the effect observed by the mutation in the PQQGDH of G. oxydans [AM. Cleton-Jansen et al., Mol. Gen Genet. (1991) 229, 206–212].

Other objects, features and advantages of the subject invention will become apparent in the course of the following description with reference to the accompanying drawings.

DESCRIPTION OF THE PREFERRED EMBODIMENTS

Figure 1:
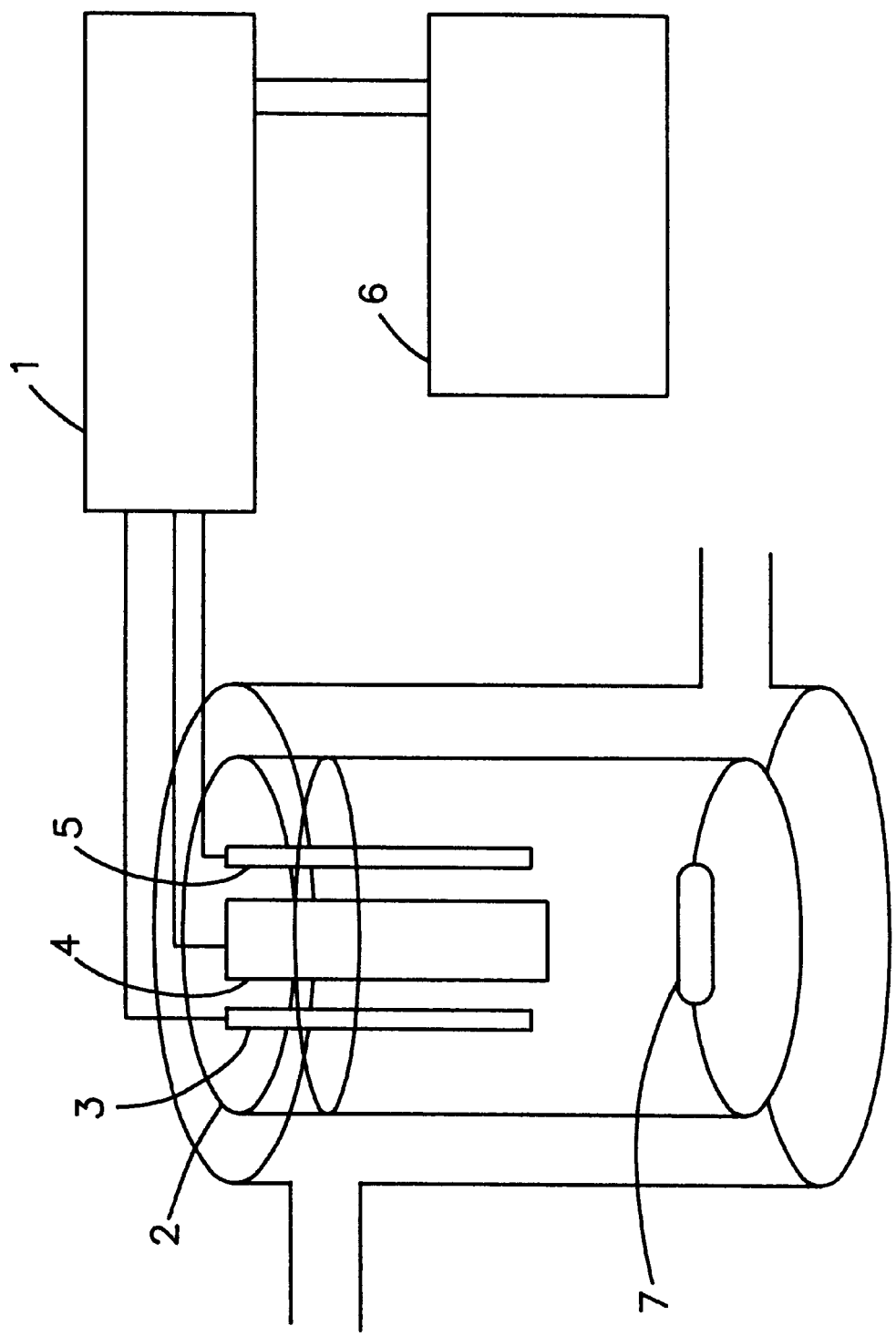
FIG. 1 illustrates a construction of a system for assaying glucose.

Structural gene of modified PQQGDH:

The structural gene of the modified enzyme of the invention has a structure wherein a base sequence encoding the histidine 775 residue in the region of the amino acids 772 to 778 (-Ala-Gly-Gly-His-Gly-Ser-Phe-) (SEQ ID NO:10) of the amino acid sequence of the conventionally reported PQQGDH of E. coli has been substituted with a base sequence encoding an amino acid residue selected from asparagine, aspartic acid, serine, tyrosine, lysine, leucine, tryptophane, glutamic acid and glutamine. These genes were constructed by substituting the base sequence encoding the histidine 775 residue in the PQQGDH gene of E. coli with base sequences each encoding an amino acid residue selected from asparagine, aspartic acid, serine, tyrosine, lysine. leucine, tryptophane, glutamic acid and glutamine using synthetic oligonucleotides. The genes thus obtained are designated to H775N. H775D, H775S, H775Y, H775K, H775L, H775W H775E and H775Q, respectively.

Process for preparing modified PQQGDHs:

The structural gene of a modified PQQGDH enzyme protein is inserted into a vector plasmid designed for gene expression, in which the histidine 775 residue in the region of the amino acids 772 to 778 (-Ala-Gly-Gly-His-Gly-Ser-Phe-) (SEQ ID NO:10) of the amino acid sequence of the PQQGDH of E. coli has been substituted with an amino acid residue selected from asparagine, aspartic acid, serine, tyrosine, lysine, leucine, tryptophane, glutamic acid and glutamine, The plasmids are transformed into E. coli, then the transformants are incubated. The cells are harvested from the culture broth by centrifugation or other means and disrupted with a French press or other means, which are then separated by ultracentrifugation to obtain a membrane fraction. The membrane fraction thus obtained is solubilized by stirring in the presence of a surfactant to give a solubilized membrane fraction. The solubilized membrane fraction thus obtained is purified by, for example, anion exchange chromatography to prepare the modified PQQGDH.

Substrate Specificity

The modified PQQGDH enzyme protein produced from the gene encoding the modified PQQGDH enzyme protein, wherein the histidine 775 residue in the region of the amino acids 772 to 778 (-Ala-Gly-Gly-His-Gly-Ser-Phe-) (SEQ ID NO:10) of the amino acid sequence of the PQQGDH of E. coli has been substituted with an amino acid residue selected from asparagine, aspartic acid, serine, tyrosine, lysine, leucine, tryptophane, glutamic acid and glutamine, differs in the substrate specificity from the conventionally reported PQQGDH of E. coli. Table 1 shows the relative activities on various saccharides, which are expressed by referring the activity on glucose as to 100. These modified PQQGDHs scarcely react with saccharides other than glucose.

Since the modified PQQGDH of the invention can react specifically with glucose, it is useful in the assay of glucose with high sensitivity and high selectivity. Moreover, this enzyme can be used in development of glucose sensors with the use of the same.

Dynamic Range

Substitution of His775 with Asp or Glu resulted not only in the increase of the substrate specificity, but also the increase in the dynamic range for glucose monitoring. H775N mutant or wild type E. coli PQQGDH show the saturated catalytic activity toward glucose concentration higher than 10 mM, while the catalytic activities of H775D and H775E increase with the increase of glucose concentrations up to 50 mM. Since this concentration covers blood glucose concentration usually found in diabetes patients (in the range of 100–300 mg/dl), a direct measurement of blood concentration can be effected using the modified enzymes H775D and H775E.

Chimera Enzymes

The improvement of substrate specificity of PQQGDH by these amino acid substitutions are not only limited to the mutation toward wild type E. coli PQQGDH. The substitutions of His775 to the amino acid residues described herein are also effective to improve the substrate specificity of PQQGDHs which harbor the corresponded sequence (Ala-Gly-Gly-His-Gly-Ser-Phe) (SEQ ID NO:10). Acinetobacter calcoaceticus is known to have the same amino acid sequence at the C-terminal region (from 778 to 784) (Cleton-Jansen et al. (1988) Nucleic Acid Res. 16, p.6228). Also, a variety of chimera PQQGDHs have been prepared (K. Sode, et al. (1995) Biochem. Biophys. Res. Commun. 211, p.268–273). Such chimera PQQGDHs contain a portion derived from E. coli PQQGDH and a portion derived from A. calcoaceticus PQQGDH functionally linked together to provide a chimera enzyme. These chimera PQQGDHs include, such as, E97A3 (3% of C-terminal region is derived from A. calcoaceticus PQQGDH and the rest of N-terminal 97% region is from E. coli PQQGDH), E32A27E41 (32% of N-terminal and 41% of C-terminal regions are derived from E. coli PQQGDH and the rest 27% is from A. calcoaceticus PQQGDH), 232A27E38A3 (32% of N-terminal region of E. coli PQQGDH, 27% from A. calcoaceticus PQQGDH, 38% from E. coli PQQGDH and the rest 3% of C-terminal region from A. calcoaceticus PQQGDH). These chimera PQQGDHs can be readily prepared in accordance with Cleton-Jansen at al. (1988) supra, and K. Sode, et al. (1995) supra; both of which are incorporated herein by reference. Some of these chimera PQQGDHs have been shown to have an improved heat-stability and/or strong binding of the enzyme portion and coenzyme portion.

In accordance with the invention, the histidine residue of PQQGDH of A. calcoaceticus and these chimera PQQGDHs corresponding to His775 of E. coli PQQGDH is substituted with another amino acid, resulted in an improvement of the substrate specificity of these enzymes.

Glucose Assay

The glucose concentration in a sample can be easily assayed using the modified PQQGDH of the invention. A sample containing glucose, for example a blood sample from a patient of diabetes, is mixed with a solution containing electron mediators, such as PMS (phenazine methosulfate) and DCIP (2,6-dichlorophenol indophenol). The modified pyrrolo-quinoline quinone glucose dehydrogenase of the invention is added to the solution, then a signal generated from the electron mediators is monitored as an indication of the glucose concentration of the sample. When PMS-DCIP are used as electron mediators, change in absorbance can be monitored at 600 nm using a spectrophotometer.

V-1200 (Shimadzu Corporation) was used in the determination.

FIG. 1 shows a system for glucose assay using the modified PQQGDH of the invention. A general constitution of such a system is well known in the art and referred to as a glucose sensor. A sensor system is composed of conventional three electrode system; a working electrode (4) with enzyme, a reference electrode (3) (Ag/AgCl) and a counter electrode (5) (Pt plate), which are connected to a potensiostat (1). In accordance with the invention, the working electrode (4) is provided with a modified PQQGDH described above. The electrodes inserted in a cell (2) provided with a stirrer (7) which contains a suitable solution, such as potassium phosphate buffer. A sample containing glucose is added to the cell, then the current can be monitored by a data processor (6) where the glucose concentration of the sample is calculated based on the value of the current.

An electrode with a modified PQQGDH can be prepared in several ways. If the enzyme electrode is being prepared from the carbon paste, enzyme electrode is constructed by packing carbon paste which contain modified PQQGDH. Such carbon paste can be prepared by 1) mixing enzyme with carbon paste resulting the adsorption of enzyme onto carbon paste, 2) mixing carbon paste with enzyme immobilized supports such as ion exchange resin or surface modified polymer matrixes. If the enzyme electrode is being prepared based on the carbon coated electrode, enzyme can be immobilized on the surface of the electrode by adsorption, or by using cross-linking reagent such as glutaraldehyde, or spread out polymer matrix, such as photocrosslinkable resin, entrapping modified PQQGDH.

The modified PQQGDH can be also immobilized onto a variety of electrode materials, such as gold and platinum, via conventional chemical modification such as using gamma aminopropyltriethoxysilan combining with glutaraldehyde. via entrapment using polymer matrix such as photo-crosslinkable resins, and/or adsorption.

EXAMPLES

The examples provided below illustrate the present invention in greater detail, but are not intended to limit the invention.

Example 1
Construction of modified PQQGDH gene

Starting from the structural gene of the PQQGDH of *E. coli* with a known structure, the base sequence encoding the histidine 775 residue was substituted with a base sequence encoding an aspartic acid, serine, tyrosine or lysine residue by the site-specific mutagenesis according to the standard technique. The following target primers were employed for mutagenesis.

H775N
5'-CC-AAA-TGA-ACC-GTT-ACC-GCC-TGC-GG-3' (SEQ ID NO. 1)
H775D
5'-CC-AAA-TGA-ACC-GTC-ACC-GCC-TGC-GG-3' (SEQ ID NO. 2)
H775S
5'-CC-AAA-TGA-ACC-GGA-ACC-GCC-TGC-GG-3' (SEQ ID NO. 3)
H775Y
5'-CC-AAA-TGA-ACC-GTA-ACC-GCC-TGC-GG-3' (SEQ ID NO. 4)
H775K
5'-CC-AAA-TGA-ACC-TTT-ACC-GCC-TGC-GG-3' (SEQ ID NO. 5)
H775L
5'-CC-AAA-TGA-ACC-GAG-ACC-GCC-TGC-GG-3' (SEQ ID NO. 6)
H775W
5'-CC-AAA-TGA-ACC-CCA-ACC-CCC-TGC-GG-3' (SEQ ID NO. 7)
H775B
5'-CC-AAA-TGA-ACC-CTC-ACC-GCC-TGC-GG-3' (SEQ ID NO. 8)
H775Q
5'-CC-AAA-TGA-ACC-CTG-ACC-GCC-TGC-GG-3' (SEQ ID NO. 9)

First, an AvaI-HindIII fragment corresponding to a part of the structural gene of the PQQGDH derived from *E. coli* DH5α [K. Sode and H. Sano, Biotechnol. Lett. (1994) 16, 455–460] was inserted into a vector plasmid pKF18k (Takara Shuzo Co., Ltd.) to provide a template. Fifty fmol of this template was mixed with 5 pmol of the selection primer supplied in Mutan-Express Km Kit (Takara Shuzo Co., Ltd.), 50 pmol of a phosphorylated target primer listed above and 1/10 volume of the whole mixture (20 ml) of the annealing buffer supplied in the kit. The plasmid was denatured by heat treatment at 100° C. for 3 minutes to give a single-stranded DNA. The target primers listed above had base sequences corresponding to the complementary strand of the gene. Namely, the region between CGT-3' on the 3'-side and 5'-AAA on the 5'-side correspond to the complementary strand of the codons from Ala772 to Phe778. The section primer served to recover the double amber mutation located on the kanamycin resistance gene of pKF18k. The reaction was placed on ice for 5 minutes to allow annealing. Then 3 ml of the extension buffer supplied in the kit, 1 ml of T4 DNA ligase, 1 ml of T4 DNA polymerase and 5 ml of sterilized water were added to the reaction to synthesize a complementary strand.

Subsequently, the plasmid was transformed into *E. coli* BMH71-18 mutS which is a strain defective of repairing DNA mismatches, and the transformant was incubated under shaking overnight to amplify the plasmid.

Next, the plasmid extracted from the culture was transformed into *E. coli* MV1184. The plasmid was extracted from the *E. coli* MV1184 colonies thus formed and sequenced to confirm the introduction of the desired mutations. Then the AvaI-HindIII fragment of the wild type PQQGDH structural gene was replaced with the fragment thus obtained to construct the gene encoding the modified PQQGDH.

Example 2
Production of modified enzyme

The structural gene of the enzyme containing the mutation was inserted into the multicloning site of an expression vector pTrc99A for *E. coli* (Pharmacia). The plasmid thus constructed was then transformed into *E. coli* PP2418 strain defective of producing PQQGDH [AM. Cleton-Jansen et al., J. Bacterial. (1990), 172, 6308–6315]. The transformant was incubated in, for example, L broth comprising 1% bactotrypton, 0.5% yeast extract and 0.5% NaCl. A 10 liter bench fermenter KMJ-10C-FPMIII (Mitsuwa Biosystem) was used. The transformant was incubated in a Sakaguchi flask containing 450 ml of L broth (containing 50 mg/ml of ampicillin and 30 mg/ml of chloramphenicol) under shaking at 37° C. overnight. Then the cells were inoculated into 7 liter of L broth containing 10 mM MgCl$_2$ and 500 μM PQQ in a fermenter. About 2 hours after the initiation of the incubation, isopropyl thiogalactoside was added so as to give a final concentration of 0.3 mM and the incubation was continued for an additional 1.5 hours. Then the cells were harvested from the culture broth by centrifugation (5000× g, 10 minutes, 4° C.) and washed twice with 0.85% NaCl solution. Next, the cells were disrupted with French press and then centrifuged (10000× g, 15 minutes, 4° C.) to remove the undisrupted cells therefrom. The supernatant was ultracentrifuged [160500× g (40000 r.p.m.), 90 minutes, 4° C.] to obtain a membrane fraction. Then 10 mM phosphate buffer (pH 7.0) containing 0.1% (w/v) Triton X-100 and 5 mM MgCl$_2$ was added at a ratio of 1 ml per 100 mg of the protein. The mixture was stirred on ice for 30 minutes to wash the membrane fraction. Then the membrane fraction was ultracentrifuged under the same conditions as those employed above. To the washed membrane fraction thus obtained, 10 mM phosphate buffer (pH 7.0) containing 0.1% (w/v) Triton X-100, 5 mM MgCl$_2$ and 0.2 M KCl were added at a ratio of 1 ml per 100 mg of the protein, and the mixture was stirred on ice for 30 minutes to solubilize the membrane fraction. The resulting mixture was ultracentrifuged to remove the insoluble components to obtain a solubilized membrane fraction. The solubilized membrane fraction thus obtained was then dialyzed against 0.1% (w/v) Triton X-100 in 10 mM phosphate buffer (pH 7.0) overnight. Next, the dialyzed sample was adsorbed to an anion exchange chromatography column TSKgel DEAE-TOYOPEARL 650 M (Tosoh Corporation) which had been equilibrated with 0.1% (w/v) Triton X-100 in 10 mM phosphate buffer (pH 7.0). After 750 ml of 1% (w/v) Triton X-100 in 10 mM phosphate buffer (pH 7.0) was passed through the column, the enzyme was eluted using 0.1% (w/v) Triton X-100 in 10 mM phosphate buffer (pH 7.0) containing 0–0.1 M KCl at a flow rate of 5 ml/min. The active fraction thus obtained was dialyzed against a 0.2% (w/v) Triton X-100 in 10 mM phosphate buffer (pH 7.0) overnight. Thus, electrophoretically homogeneous modified PQQGDH protein was obtained.

the mixture, 3 ml of an activation reagent (48 ml of 6 mM DCIP, 8 ml of 600 mM PMS and 16 ml of 0.2% Triton in 10 mM phosphate buffer, pH 7.0) and 10 ml of a substrate solution of the indicated concentration were added. The enzyme activity was determined by the method as described in Example 3.

Example 5

Glucose assay

Figure 2:
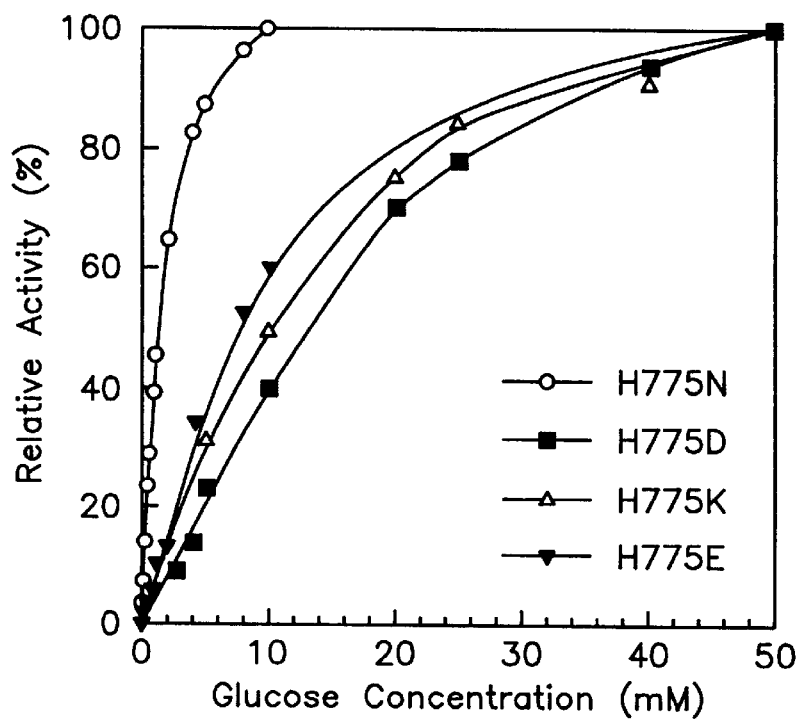
FIG. 2 is a graph showing the relation between the enzyme activity of the modified PQQGDHs according to the invention and the glucose concentration.

FIG. 2 shows the results of the glucose assay using the modified PQQGDH. The assay of enzyme activity was performed in the similar manner as described above by monitoring changes in the absorbance of DCIP at 600 nm as an indication. As shown in FIG. 2. glucose can be assayed using the modified PQQGDH of the invention.

TABLE 1

Substrate specificity of the modified enzymes

| | | Relative activity (%) | | | | | |
|---|---|---|---|---|---|---|---|
| Substrate | PQQGDH of E. coli | H775N | H775D | H775K | H775L | H775W | H775E |
| D-glucose | 100 | 100 | 100 | 100 | 100 | 100 | 100 |
| D-mannose | 30 | 1 | 0 | 0 | 36 | 57 | 1 |
| D-galactose | 38 | 2 | 0 | 6 | 2 | 2 | 2 |
| D-xylose | 48 | 4 | 1 | 16 | 3 | 10 | 2 |
| maltose | 14 | 5 | 3 | 23 | 2 | 4 | 0 |

Example 3

Determination of enzyme activity

The enzyme activity was determined using PMS (phenazine methasulfate)-DCIP (2,6-dichlorophenol indophenol) in 10 mM phosphate buffer (pH 7.0) containing 0.2% (w/v) Triton X-100. Changes in the absorbance of DCIP at 600 nm was monitored, and the decreasing rate of the absorbance was referred to as the reaction rate of the enzyme. The enzyme activity by which 1 mmol of DCIP was reduced in 1 minutes was defined as 1 U. The molar absorption coefficient of DCIP at pH 7.0 was 16.3 mM$^{-1}$. A spectro-photometer UV-1200 (Shimadzu Corporation) was used in the determination.

Example 4

Determination of substrate specificity

An appropriate amount of the purified enzyme was converted into a holoenzyme in the presence of 5 mM PQQ and 10 MM MgCl$_2$ over 1 hour or longer. To 187 ml aliquots of Example 6

Construction of glucose sensor

A carbon paste electrode (CPE, internal diameter 3 mm; BAS Co. USA) was packed with carbon paste (BAS Co. USA). About 1 mm depth of the surface carbon paste was removed and replaced with PQQGDH modified carbon paste, which is prepared by mixing 10 mg of carbon paste with 14 units of modified PQQGDH in a 10 mM potassium phosphate buffer, and was subsequently lyophilized.

Figure 3:
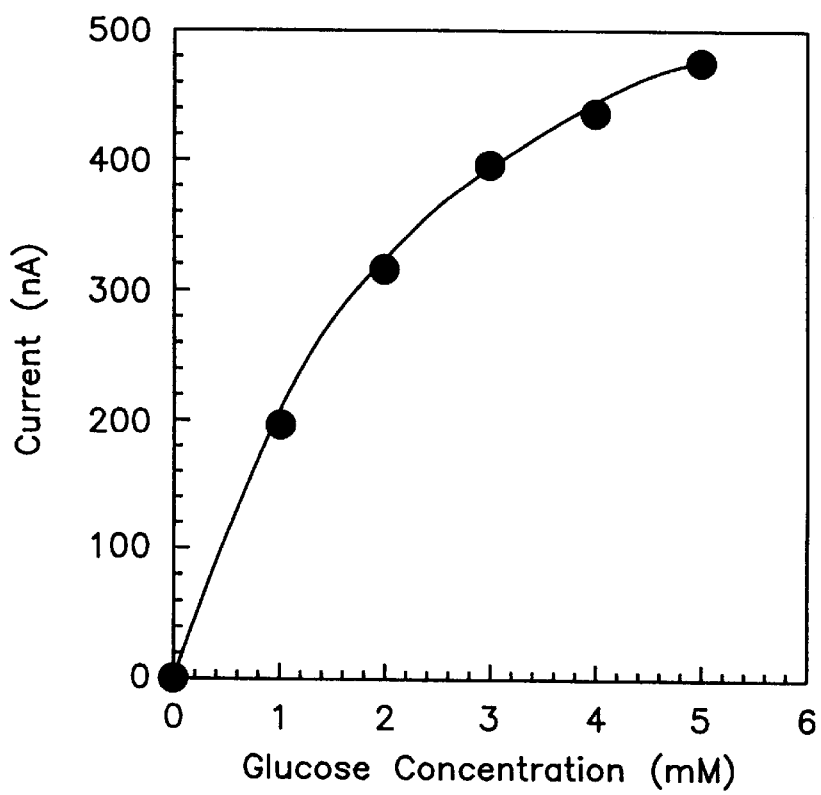
FIG. 3 is a calibration curve of the glucose sensor of the invention.

Enzyme sensor system is composed of conventional three electrode system; a working electrode with modified PQQGDH, a reference electrode (Ag/AgCl, BAS Co. USA) and a counter electrode (5) (Pt plate). All measurements are carried out at 25° C. in 10 ml of 100 mM potassium phosphate buffer solution (pH 7.0) containing 5 μM PQQ, 1 mM MgCl$_2$ and 2 mM PMS as an electron mediator. The anodic potential for the mediated electrolytic oxidation of PMS is set at +70 mM vs Ag/AgCl. With the addition of glucose solution, the anodic current gradually increased and reached a steady state in 20 to 30 sec. The correlation between glucose concentration and current increase is demonstrated in FIG. 3. FIG. 3 shows the result of the glucose sensor employing H775N enzyme of the invention.

What is claimed is:

1. A pyrrolo-quinoline quinone glucose dehydrogenase (PQQGDH) enzyme comprising the amino acid sequence Ala-Gly-Gly-Xaa-Gly-Ser-Phe (SEQ ID No:11), wherein said Xaa residue is any amino acid residue other than histidine, wherein said SEQ ID No:11 is found in a region corresponding to the sequence Ala-Gly-Gly-His-Gly-Ser-Phe (SEQ ID No:10) found in wild-type *E. coli* PQQGDH, and wherein said PQQGDH enzyme has increased substrate specificity to glucose compared to that of said wild-type *E. coli* PQQGDH that comprises SEQ ID No:10.

2. The enzyme claimed in claim 1 wherein said Xaa residue is selected from the group consisting of asparagine, aspartic acid, serine, tyrosine, lysine, leucine, tryptophane, glutamic acid and glutamine.

3. The enzyme claimed in claim 2 wherein said Xaa residue is aspartic acid or glutamic acid.

4. The enzyme claimed in claim 1 which is a chimeric protein.

5. An isolated polynucleotide encoding the PQQGDH enzyme of claim 1.

6. The polynucleotide claimed in claim 5 wherein said Xaa residue is selected from the group consisting of asparagine, aspartic acid, serine, tyrosine, lysine, leucine, tryptophane, glutamic acid and glutamine.

7. The polynucleotide claimed in claim 6 wherein said Xaa residue is aspartic acid or glutamic acid.

8. The polynucleotide claimed in claim 5 wherein said enzyme is a chimeric protein.

9. A plasmid containing the polynucleotide claimed in claim 5.

10. A transformant comprising the plasmid claimed in claim 9.

11. A kit for assaying glucose in a sample, the kit comprising the PQQGDH enzyme of claim 1 and suitable reagents.

* * * * *

SEQUENCE LISTING

<160> NUMBER OF SEQ ID NOS: 11

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Target
      Primer

<400> SEQUENCE: 1
ccaaatgaac cgttaccgcc tgcgg                                          25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Target
      Primer

<400> SEQUENCE: 2
ccaaatgaac cgtcaccgcc tgcgg                                          25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Target
      Primer

<400> SEQUENCE: 3
ccaaatgaac cggaaccgcc tgcgg                                          25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Target
      Primer

<400> SEQUENCE: 4
ccaaatgaac cgtaaccgcc tgcgg                                          25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Target
      Primer

<400> SEQUENCE: 5
ccaaatgaac ctttaccgcc tgcgg                                          25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Target
      Primer

<400> SEQUENCE: 6

```
ccaaatgaac cgagaccgcc tgcgg                                         25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Target
      Primer

<400> SEQUENCE: 7
ccaaatgaac cccaaccgcc tgcgg                                         25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Target
      Primer

<400> SEQUENCE: 8
ccaaatgaac cctcaccgcc tgcgg                                         25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Target
      Primer

<400> SEQUENCE: 9
ccaaatgaac cctgaccgcc tgcgg                                         25

<210> SEQ ID NO 10
<211> LENGTH: 7
<212> TYPE: PRT
<213> ORGANISM: Escherichia coli

<400> SEQUENCE: 10

Ala Gly Gly His Gly Ser Phe
 1               5

<210> SEQ ID NO 11
<211> LENGTH: 7
<212> TYPE: PRT
<213> ORGANISM: Escherichia coli
<220> FEATURE:
<223> OTHER INFORMATION: Xaa can be anything except His

<400> SEQUENCE: 11

Ala Gly Gly Xaa Gly Ser Phe
 1               5
```